United States Patent [19]

Wagner

[11] 4,405,780
[45] Sep. 20, 1983

[54] 8-SUBSTITUTED 7-PHENYL-1,2,4,-TRIAZOLO[4,3-C]/[2,3-C]PYRIMIDINES-5-AMINES AND AMIDES

[75] Inventor: Hans Wagner, Skokie, Ill.

[73] Assignee: G. D. Searle & Co., Skokie, Ill.

[21] Appl. No.: 352,913

[22] Filed: Feb. 26, 1982

Related U.S. Application Data

[63] Continuation-in-part of Ser. No. 64,707, Aug. 8, 1979, abandoned.

[51] Int. Cl.$^3$ .............. C07D 487/04; A61K 31/505
[52] U.S. Cl. ........................ 544/263; 424/251; 544/323; 544/325; 544/332
[58] Field of Search ........................ 544/263

[56] References Cited

U.S. PATENT DOCUMENTS 3,046,276 7/1962 Miller et al. ................ 544/263
3,053,844 9/1962 Miller et al. ................ 544/263

FOREIGN PATENT DOCUMENTS 1205144 1/1960 France ........................ 544/263
52578 9/1959 United Kingdom ........... 544/263

OTHER PUBLICATIONS

Shirakawa, "Chemical Abstracts," vol. 54, (1960), Col. 24761h–24763i.

Primary Examiner—Donald G. Daus
Assistant Examiner—James H. Turnipseed
Attorney, Agent, or Firm—James G. Passe'

[57] ABSTRACT

This invention relates to compounds having the formula

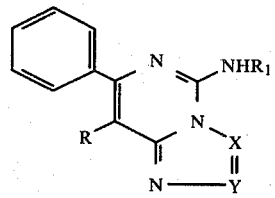

wherein R represents hydrogen, alkyl containing one to four carbon atoms, or alkoxyalkyl, alkenyl or alkynyl containing two to four carbon atoms, $R_1$ represents hydrogen or 1-oxoalkyl containing one to two carbon atoms and wherein X and Y are carbon or nitrogen with the proviso that one of X and Y must be nitrogen and the other carbon and which are useful diuretic agents.

11 Claims, No Drawings

8-SUBSTITUTED 7-PHENYL-1,2,4,-TRIAZOLO[4,3-C]/[2,3-C]PYRIMIDINES-5-AMINES AND AMIDES

SUMMARY OF INVENTION

This application is a continuation-in-part of application Ser. No. 06/064,707 filed Aug. 8, 1979, now abandoned.

This invention relates to a 8-substituted-7-phenyl-1,2,4-triazolo[4,3-c]pyrimidine-5-amines and amides and to 8-substituted-7-phenyl-1,2,4-triazolo[2,3-c]pyrimidine-5-amines and amides and the process for their preparation. More particularly, this invention provides new, useful and unobvious chemical compounds of formula II of Chart A, wherein R represents hydrogen, alkyl containing one to four carbon atoms, or alkoxyalkyl, alkenyl or alkynyl containing two to four carbon atoms, $R_1$ represents hydrogen or 1-oxoalkyl containing one to two carbon atoms and wherein X and Y are carbon or nitrogen with the proviso that one of X and Y must be nitrogen and the other carbon.

Those alkyl radicals containing one to four carbon atoms and represented by R are typified by methyl, ethyl, propyl and butyl and the corresponding branched-chain isomers.

Those alkoxyalkyl radicals containing two to four carbon atoms and represented by R are typified by methoxymethyl, 1-methoxyethyl, 2-methoxyethyl, 2-methoxypropyl, 3-methoxypropyl, 1-ethoxyethyl, 2-ethoxyethyl, ethoxymethyl, propoxymethyl and (1-methylethoxy)methyl.

Those alkenyl and alkynyl radicals containing two to four carbon atoms and represented by R are typified by phenyl, 1-propenyl, 2-propenyl, 1-butynyl, 2-butynyl, and 3-butynyl and the corresponding branched-chain isomers.

The 1-oxoalkyl radicals containing one to two carbon atoms and represented by $R_1$ are Formyl and acetyl.

Embodiments of the present invention wherein $R_1$ is hydrogen are preferred. The embodiment represented by R equal to alkyl containing one to four carbon atoms and alkoxyalkyl containing one to four carbon atoms are especially preferred.

The compounds of this invention are useful because of their valuable pharmacological properties. Thus, for example, they are potent diuretics: when assayed for the capacity to increase urine volume as described by Lipschitz et al. [J. Pharmacol. Exp., Therap., 79 97 (1943)] and assigned potencies based upon paralled dose response curves in accordance with Finney [*Statistical Method in Biological Assay*, 2nd. ed., Charles Griffin & Company, Limited, London, 1964], for example, 8-methyl-7-phenyl-1,2,4-triazolo[2,3-c]pyrimidine-5-amine and 8-(2-ethoxyethyl)-7-phenyl-1,2,4-triazolo[2,3-c]pyrimidine-5-amine were found to be 1.2 and 2.7 times as potent as hydrochlorothiazide, respectively. The typical dosage of hydrochlorothiazide as a diuretic for use in humans is 25 or 50 mg per oral administration.

For therapeutic purposes, the compounds of this invention are ordinarily combined with one or more adjuvants appropriate to the indicated route of administration. If per os, they may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia, sodium alginate, polyvinylpyrrolidone, and/or polyvinyl alcohol, and thus tableted or encapsulated for convenient administration; alternatively, they may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art; see, for example, F. W. Martin et al, *Remington's Pharmaceutical Sciences*, 14th ed., Merck Publishing Co., Eaton, Pa., 1965.

Appropriate dosages, in any given instance, of course depend upon the nature and severity of the condition treated, the route of administration, and the species of mammal involved, including its size and any individial idosyncrasies.

DESCRIPTION OF INVENTION

The compounds of this instant invention can be made via the methods described herein and as outlined on Charts A and B. There will be other methods to make the compounds obvious to those skilled in the art and the methods herein are included by way of example and general description and the practice of this invention should not be limited to the methods described in the general description.

Both the [4,3-c] and [2,3-c] amines of this invention can be prepared by contacting 4-chloro-6-phenyl-pyrimidin-2-amines of formula I (wherein R is defined as above and wherein $R_2$ is hydrogen) with formylhydrazine in dimethylformamide. The resulting amines can be crystallized or chromatographed.

Both the [4,3-c] and [2,3-c] amides of this invention can be prepared by contacting the corresponding amines of this invention with acetic anhydride or acetic formic anhydride, depending upon the desired amide.

Both the [4,3-c] amides and amines can be further heated to yield the corresponding [2,3-c] compounds respectively, as described in Chart B.

An alternative process for the preparation of the [4,3-c] and [2,3-c] amides of this invention is to contact the appropriate N-(4-chloro-6-phenylpyrimidin-2-yl)amide of formula I of Chart A, (wherein R is defined as above and $R_2$ is a formyl or acetyl radical) with formylhdrazine in dimethylformamide. The solid product is formed with the addition of water yielding a mixture of the [4,3-c] and [2,3-c] amides.

The following examples describe in detail compounds illustrative of the present invention and methods for their preparation. However, the invention is not to be construed as limited by the examples since it will be apparent to those skilled in the art of organic synthesis that many modifications, both of materials and methods, may be practiced without departing from the purpose and intent of this disclosure. Throughout the examples, temperatures are given in degrees centigrade and relative amounts of materials in parts by weight, except as otherwise noted.

DESCRIPTION OF THE PREFERRED EMBODIMENTS

EXAMPLE 1

5.5 Parts of 4-chloro-5-methyl-6-phenylpyrimidin-2-amine and 3.0 parts of formylhydrazine are added to 50 parts by volume dimethylformamide containing 5.0 parts of molecular sieve 3A and refluxed under nitrogen for two hours. After standing for 16 hours at room temperature the solution is poured into cold water. The crystalline product is filtered out, washed with water and dried. The product is chromatographed to yield, 8-methyl-7-phenyl-1,2,4-triazolo[4,3-c]pyrimidin-5-amine having the formula:

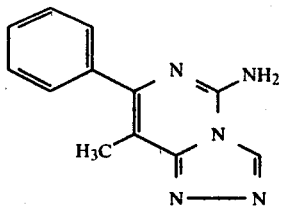

and the 8-methyl-7-phenyl-1,2,4-triazolo[2,3-c]pyrimidin-5-amine having the formula:

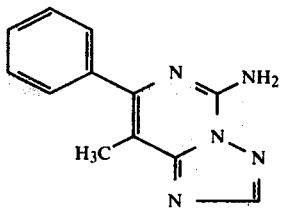

EXAMPLE 2

10.0 Parts of 4-chloro-5-(2-ethoxyethyl)-6-phenylpyrimidin-2-amine and 3.0 parts of formylhydrazine are added to 80 parts by volume dimethylformamide containing 8.0 parts of molecular sieve 3A and refluxed under nitrogen for two hours. After standing for 16 hours at room temperature the solution is poured into cold water. The product is chromatographed to give a mixture of 8-(2-ethoxyethyl)-7-phenyl-1,2,4-triazolo[4,3-c]pyrimidin-5-amine having the formula:

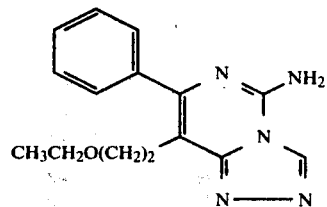

and 8-(2-ethoxyethyl)-7-phenyl-1,2,4-triazolo[2,3-c]pyrimidin-5-amine having the formula:

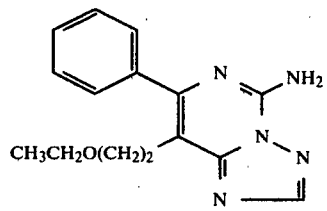

EXAMPLE 3

1.7 Parts of 4-chloro-6-phenyl-5-(2-propynyl)pyrimidin-2-amine and 0.84 part of formylhydrazine are added to 20 parts by volume dimethylformamide containing 2.0 parts of molecular sieve 3A and refluxed under nitrogen for two hours. The solution is allowed to cool and is poured into cold water. The crystalline product is filtered out, washed with water and dried. The product is chromatographed to give 7-phenyl-8-(2-propynyl)-1,2,4-triazolo[4,3-c]pyrimidin-5-amine having the formula:

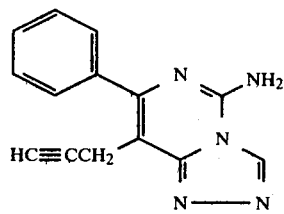

and 7-phenyl-8-(2-propynyl)-1,2,4-triazolo[2,3-c]pyrimidine-5-amine having the formula:

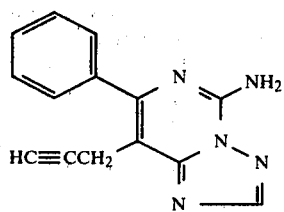

EXAMPLE 4

6.6 Parts of 8-methyl-7-phenyl-1,2,4-triazolo[2,3-c]pyrimidin-5-amine (Example 1) is suspended in 50 parts by volume pyridine and 10 parts by volume acetic anhydride. The solution is stirred at room temperature for approximately 18 hours until a clear solution is formed. After approximately 21 hours turbidity develops and a solid gradually forms. After standing for approximately 40 hours most of the solvent is removed in vacuo. The residue is stirred in water, filtered, washed with water and dried. The product is recrystallized from methanol to give N-[8-methyl-7-phenyl-1,2,4-triazolo[2,3-c]pyrimidin-5-yl]acetamide having the formula:

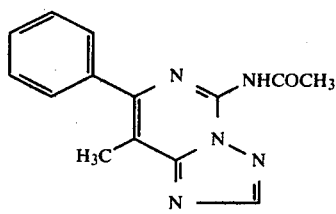

EXAMPLE 5

An alternative process for synthesizing the product N-[8-methyl-7-phenyl-1,2,4-triazolo[2,3-c] or [4,2-c]pyrimidine-5-yl]acetamide of Example 4 is to start with the appropriate chlorinated pyrimidine. 7.85 Parts of N-(4-chloro-5-methyl-6-phenylpyrimidin-2-yl)acetamide having the formula:

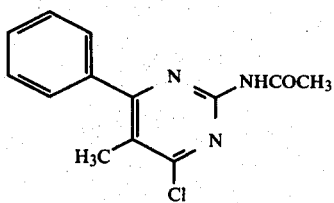

is added to 6.0 parts of formylhydrazine and 60 parts by volume dimethylformamide. The solution is heated to reflux under nitrogen for 2.5 hours. The solution is allowed to cool and stand at room temperature for 16 hours. The clear solution is poured into cold water, with stirring. A crystalline material is formed. The material is filtered, washed with water, dried, and chromatographed to give the desired products.

EXAMPLE 6

6.4 Parts of N-[4-chloro-5-(2-ethoxyethyl)-6-phenyl-primidin-2-yl]acetamide and 2.4 parts of formylhydrazine are added to 60 parts by volume dimethylformamide containing 6.0 parts of molecular sieve 3A and refluxed under nitrogen for one hour. The solution is then allowed to cool. The solution yields the following products N-[8-(2-ethoxyethyl)-7-phenyl-1,2,4-triazolo[4,3-c]pyrimidin-2-yl]acetamide having the formula:

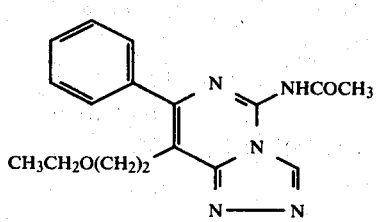

and N-[8-(2-ethoxyethyl)-7-phenyl-1,2,4-triazolo[2,3-c]pyrimidin-2-yl]acetamide having the formula:

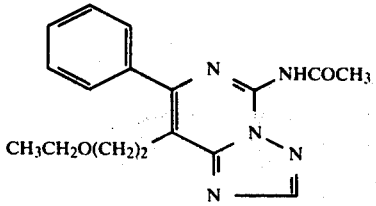

EXAMPLE 7

A solution of 6.39 g (23.0 mmoles) of 4-chloro-5-ethyl-6-phenylpyrimidin-2-amine in 30 ml of 100% of hydrazine hydrate and 40 ml of ethanol is refluxed for one hour. The solution is poured into 400 ml of water and the resulting solution is saturated with sodium chloride and cooled in an ice bath. The solid product is collected by filtration, washed with water and dried in a vacuum to give 4.94 g of a solid having a melting point of 127°–129° C.

A solution of 1.27 g (4.65 mmoles) of the solid in 15 ml of triethylene glycol dimethyl ether (triglyme) is treated with 0.74 g (5.00 mmoles) of triethyl orthoformate and the resulting solution is heated at 140° C. for 1 hour. The solution is cooled to room temperature and poured into 60 ml of water. The solid formed is collected by filtration, washed with water, air dried and recrystallized from methanol/ethyl acetate to give 8-(2-ethoxyethyl)-7-phenyl-1,2,4-triazolo[4,3-c]pyrimidin-5-amine which may be further treated to yield 8-(2-ethoxyethyl)-7-phenyl-1,2,4-triazolo[2,3-c]pyrimidin-5-amine by dissolving 1.13 g (4.00 mmoles) in 10 ml of triethylene glycol dimethyl ether (triglyme) and heating to reflux at 216° C. for 1 hour. The solution is cooled to room temperature and poured into 50 ml of water.

The aqueous phase is saturated with sodium chloride and cooled in an ice bath. The solid product is collected by filtration and recrystallized from methanol.

CHART A

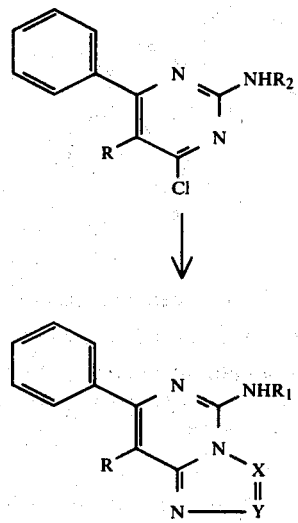

CHART B

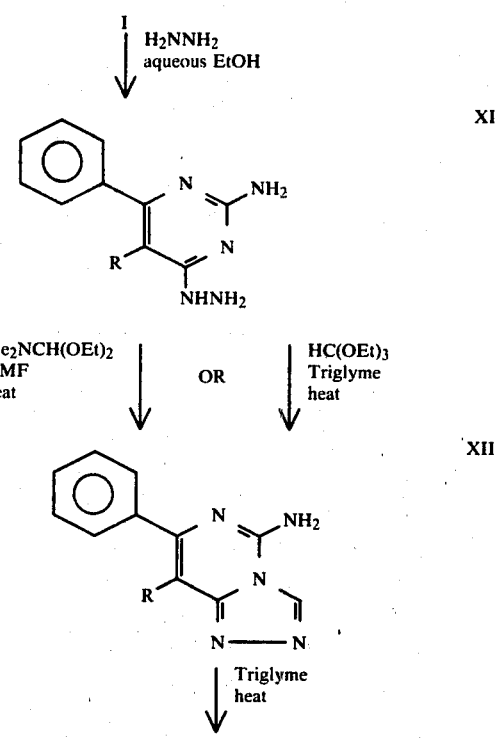

-continued

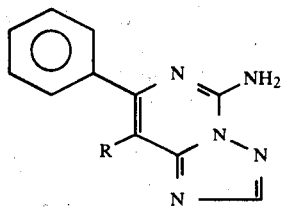

What is claimed is:

1. A compound of the formula

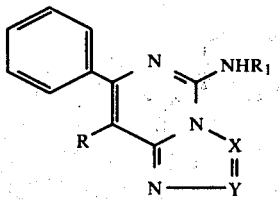

wherein R is:
(a) hydrogen
(b) alkyl having 1 to 4 carbon atoms;
(c) alkoxyalkyl having 2 to 4 carbon atoms;
(d) alkenyl having 2 to 4 carbon atoms; or
(e) alkynyl having 2 to 4 carbon atoms;
wherein $R_1$ is:
(a) hydrogen
(b) 1-oxoalkyl having 1 to 2 carbon atoms;

wherein X and Y are carbon or nitrogen with the proviso that one of X and Y must be nitrogen and the other carbon.

2. A compound according to claim 1 wherein R is of the formula R"OR'— and
wherein R' is:
(a) alkylene having 1 to 2 carbon atoms;
wherein R" is:
(a) alkyl having 1 to 2 carbon atoms;
wherein $R_1$ is:
(a) hydrogen; or
(b) 1-oxoalkyl having 1 to 2 carbon atoms.

3. A compound according to claim 2 wherein $R_1$ is hydrogen.

4. 8-(2-ethoxyethyl)-7-phenyl-1,2,4-triazolo[2,3-c]pyrimidin-5-amine, a compound according to claim 3.

5. 8-(2-ethoxyethyl)-7-phenyl-1,2,4-triazolo[4,3-c]pyrimidin-5-amine, a compound according to claim 3.

6. A compound according to claim 1 wherein $R_1$ is hydrogen and
wherein R is:
(a) hydrogen;
(b) methyl or ethyl;
(c) ethenyl; or
(d) ethynyl.

7. 8-methyl-7-phenyl-1,2,4-triazolo[2,3-c]pyrimidin-5-amine, a compound according to claim 6.

8. 8-methyl-7-phenyl-1,2,4-triazolo[4,3-c]pyrimidin-5-amine, a compound according to claim 6.

9. A compound according to claim 2 wherein $R_1$ is 1-oxoalkyl having 1 to 2 carbon atoms.

10. N-[8-methyl-7-phenyl-1,2,4-triazolo[4,3-c]pyrimidin-5-yl]acetamide, a compound according to claim 9.

11. N-[8-methyl-7-phenyl-1,2,4-triazolo[2,3-c]pyrimidin-5-yl]acetamide, a compound according to claim 9.

* * * * *